(12) United States Patent
Suddaby

(10) Patent No.: US 11,701,240 B2
(45) Date of Patent: Jul. 18, 2023

(54) EXPANDABLE INTERVERTEBRAL FUSION IMPLANT

(71) Applicant: Loubert S. Suddaby, Orchard Park, NY (US)

(72) Inventor: Loubert S. Suddaby, Orchard Park, NY (US)

(*) Notice: Subject to any disclaimer, the term of this patent is extended or adjusted under 35 U.S.C. 154(b) by 216 days.

(21) Appl. No.: 17/179,902

(22) Filed: Feb. 19, 2021

(65) Prior Publication Data

US 2022/0265436 A1    Aug. 25, 2022

(51) Int. Cl.
*A61F 2/44* (2006.01)
*A61F 2/30* (2006.01)

(52) U.S. Cl.
CPC ...... *A61F 2/447* (2013.01); *A61F 2002/3054* (2013.01); *A61F 2002/30266* (2013.01); *A61F 2002/30331* (2013.01); *A61F 2002/30471* (2013.01); *A61F 2002/30579* (2013.01); *A61F 2002/30593* (2013.01); *A61F 2002/30622* (2013.01)

(58) Field of Classification Search
CPC .......... A61F 2/44; A61F 2/442; A61F 2/4455; A61F 2/4611; A61F 2/447; A61F 2002/30266; A61F 2002/30331; A61F 2002/30471; A61F 2002/3054; A61F 2002/30579; A61F 2002/30593; A61F 2002/30622
USPC ........................................... 623/17.11–17.16
See application file for complete search history.

(56) References Cited

U.S. PATENT DOCUMENTS

| | | | |
|---|---|---|---|
| 6,174,334 B1* | 1/2001 | Suddaby | A61F 2/4455 623/17.11 |
| 6,193,757 B1 | 2/2001 | Foley et al. | |
| 6,395,031 B1 | 5/2002 | Foley et al. | |
| 6,491,724 B1* | 12/2002 | Ferree | A61F 2/447 623/17.11 |
| 6,833,006 B2 | 12/2004 | Foley et al. | |
| 7,044,971 B2* | 5/2006 | Suddaby | A61F 2/4455 623/17.11 |
| 7,087,055 B2 | 8/2006 | Lim et al. | |
| 7,655,042 B2 | 2/2010 | Foley et al. | |
| 7,931,674 B2 | 4/2011 | Zucherman et al. | |
| 7,993,403 B2 | 8/2011 | Foley et al. | |
| 8,628,577 B1* | 1/2014 | Jimenez | A61F 2/442 623/17.15 |

(Continued)

FOREIGN PATENT DOCUMENTS

| | | |
|---|---|---|
| CN | 202568533 | 12/2012 |
| WO | WO 2013/173767 | * 11/2013 |

*Primary Examiner* — Jessica Weiss
(74) *Attorney, Agent, or Firm* — Harter Secrest & Emery LLP; Michael Nicholas Vranjes

(57) ABSTRACT

An expandable intervertebral fusion implant, including an inferior component, including a first horizontal member, a first vertical member connected to the first horizontal member, and a first outward facing surface, a superior component hingedly connected to the inferior component, the superior component including a second horizontal member, a second vertical member connected to the second horizontal member, and a second outward facing surface directed away from the first outward facing surface, a first shell hingedly connected to the inferior component, and a first wedging component slidingly arranged between the first shell and the first outward facing surface.

20 Claims, 11 Drawing Sheets

(56) References Cited

U.S. PATENT DOCUMENTS

| | | | |
|---|---|---|---|
| 9,393,130 B2 * | 7/2016 | Suddaby | A61F 2/46 |
| 9,402,658 B2 | 8/2016 | Dinville et al. | |
| 9,566,163 B2 | 2/2017 | Suddaby et al. | |
| 9,913,667 B2 | 3/2018 | Dinville et al. | |
| 10,080,666 B2 | 9/2018 | Suddaby et al. | |
| 10,426,633 B2 * | 10/2019 | Moskowitz | A61F 2/4611 |
| 10,470,895 B2 * | 11/2019 | Suddaby | A61F 2/447 |
| 10,492,923 B2 | 12/2019 | Zur et al. | |
| 10,517,652 B2 | 12/2019 | Dinville et al. | |
| 10,548,740 B1 * | 2/2020 | Abdou | A61F 2/4611 |
| 10,973,650 B2 * | 4/2021 | Stein | A61F 2/4611 |
| 11,026,805 B2 * | 6/2021 | Suddaby | A61F 2/447 |
| 11,234,833 B2 * | 2/2022 | Brotman | A61F 2/4455 |
| 2006/0271194 A1 | 11/2006 | Zucherman et al. | |
| 2014/0018922 A1 * | 1/2014 | Marino | A61F 2/447 |
| | | | 623/17.16 |

\* cited by examiner

EXPANDABLE INTERVERTEBRAL FUSION IMPLANT

FIELD

The present disclosure relates to orthopedic surgery, and more particularly to an expandable and deployable intervertebral fusion implant capable of being placed within an intervertebral disc space and expanded.

BACKGROUND

The spinal column, or backbone, is one of the most important parts of the body. It provides the main support, allowing us to stand upright, bend, and twist. As shown in FIG. 1, thirty three (33) individual bones interlock with each other to form the spinal column. The vertebrae are numbered and divided into regions. The cervical vertebrae C1-C7 form the neck, support the head and neck, and allow nodding and shaking of the head. The thoracic vertebrae T1-T12 join with the ribs to form the rib cage. The five lumbar vertebrae L1-L5 carry most of the weight of the upper body and provide a stable center of gravity when a person moves. Five vertebrae of the sacrum S and four of the coccyx C are fused. This comprises the back wall of the pelvis. Intervertebral discs are located between each of the mobile vertebra. Intervertebral discs comprise a thick outer layer with a crisscrossing fibrous structure annulus A that surrounds a soft gel-like center, the nucleus N. Discs function like shock-absorbing springs. The annulus pulls the vertebral bodies together against the elastic resistance of the gel-filled nucleus. When we bend, the nucleus acts like a ball bearing, allowing the vertebral bodies to roll over the incompressible gel. Each disc works in concert with two facet joints, forming a spinal motion segment. The biomechanical function of each pair of facet joints is to guide and limit the movement of the spinal motion segment. The surfaces of the joint are coated with cartilage that helps each joint move smoothly. Directly behind the discs, the ring-like vertebral bodies create a vertical tunnel called the spinal canal or neuro canal. The spinal cord and spinal nerves pass through the spinal canal, which protects them from injury. The spinal cord is the major column of nerve tissue that is connected to the brain and serves as an information super-highway between the brain and the body. The nerves in the spinal cord branch off to form pairs of nerve roots that travel through the small openings between the vertebrae and the intervertebral foramens.

Various medical conditions require a surgeon to repair, remove and/or replace the aforementioned discs. For example, in one surgical procedure, known as a discectomy (or diskectomy) with interbody fusion, the surgeon removes the nucleus of the disc and replaces it with an implant. As shown in FIG. 2, it may be necessary, for example, for the surgeon to remove the nucleus of the disc between the L3 and L4 vertebrae. Disc $D_{L3-L4}$ is shown in an enlarged view in FIG. 3. This figure also shows various anatomical structures of the spine, including facets F3A and F4A, facet joint FJ, spinous processes SP3 (not shown) and SP4, transverse processes TP3A and TP4A, and intervertebral foramen IF. FIG. 4 is a top view of the section of the spinal column shown in FIG. 3, with the L3 vertebra removed to expose annulus A and nucleus N of disc $D_{L3-L4}$. Neural canal NC is also shown. FIG. 5 is an anterior perspective view of the section of the spinal column shown in FIG. 4. FIG. 6 is a partial cross-sectional view of the section of the spinal column shown in FIG. 5, taken generally along line 6-6, but with vertebra L3 in place atop disc $D_{L3-L4}$.

Of all animals possessing a backbone, human beings are the only creatures who remain upright for significant periods of time. From an evolutionary standpoint, this erect posture has conferred a number of strategic benefits, not the least of which is freeing the upper limbs for purposes other than locomotion. From an anthropologic standpoint, it is also evident that this unique evolutionary adaptation is a relatively recent change, and as such has not benefitted from natural selection as much as have backbones held in a horizontal attitude. As a result, the stresses acting upon the human backbone (or "vertebral column"), are unique in many senses, and result in a variety of problems or disease states that are peculiar to the human species.

The human vertebral column is essentially a tower of bones held upright by fibrous bands called ligaments and contractile elements called muscles. There are seven bones in the neck or cervical region, twelve in the chest or thoracic region, five in the lower back or lumbar region, and five in the pelvic or sacral region, which are normally fused together to form the back part of the pelvis. This column of bones is critical for providing structural support for the entire body.

Between the vertebral bones themselves exist soft tissue structures, i.e., discs, composed of fibrous tissue and cartilage that are compressible and act as shock absorbers for sudden downward forces on the upright column. The discs allow the bones to move independently of each other, as well. The repetitive forces which act on these intervertebral discs during repetitive activities of bending, lifting, and twisting cause them to break down or degenerate over time.

Presumably, because of humans' upright posture their intervertebral discs have a high propensity to degenerate. Overt trauma or covert trauma, occurring in the course of repetitive activities, disproportionately affects the more highly mobile areas of the spine. Disruption of a disc's internal architecture leads to bulging, herniation, or protrusion of pieces of the disc and eventual disc space collapse. Resulting mechanical and even chemical irritation of surrounding neural elements (spinal cord and nerves) cause pain, attended by varying degrees of disability. In addition, loss of disc space height relaxes tension on the longitudinal spinal ligaments, thereby contributing to varying degrees of spinal movement.

The time-honored method of addressing the issues of neural irritation and instability resulting from severe disc damage has largely focused on removal of the damaged disc and fusing the adjacent vertebral elements together. Removal of the disc relieves the mechanical and chemical irritation of neural elements, while osseous union (i.e., bone knitting) solves the problem of stability.

While cancellous bone appears ideal to provide the biologic components necessary for osseous union to occur, it does not initially have the strength to resist the tremendous forces that may occur in the intervertebral disc space, nor does it have the capacity to adequately stabilize the spine until long term bony union occurs. For these reasons, many spinal surgeons have found that interbody fusion using bone alone has an unacceptably high rate of bone graft migration or even expulsion or nonunion due to structural failure of the bone or residual degrees of motion that retard or prohibit bony union. Intervertebral prosthesis in various forms has therefore been used to provide immediate stability and to protect and preserve an environment that fosters growth of the grafted bone such that a structurally significant bony fusion can occur.

Limitations of most present-day intervertebral implants are significant and revolve largely around the marked variation in the disc space height and shape that result from either biologic variability or pathologic change. For example, if a disc space is 20 mm in height, a circular implant bridging this gap requires a minimum diameter of 20 mm just to contact the end plate of the vertebral bone. Generally, end plate disruption must occur to allow a generous bony union, meaning that an additional 2-3 mm must be added on either side resulting in a final implant size of 24-26 mm. During implantation from an anterior approach (i.e., from the front of the body), excessive retraction (or pulling) is often required on the great blood vessels, which greatly enhances the risk of devastating complications such as vascular tears or thrombosis. On the other hand, during a posterior approach, large implant diameters may require excessive traction on neural elements for adequate placement, even if all posterior bony elements are removed. In some instances, an adequate implant size cannot be inserted posteriorly, particularly if there is a significant degree of distraction to obtain stability by tightening the annular ligamentous tension band. Compromising on implant size risks sub-optimal stability or a loose implant, which has a greater risk of migration within, or expulsion from, the disc space. The alternative of excessively retracting neural elements to facilitate a posterior implant application results in a neuropraxia at best and permanent neural damage at worst.

Thus, there is a long-felt need for an expandable and deployable intervertebral fusion implant capable of being placed within an intervertebral disc space and expanded.

SUMMARY

According to aspects illustrated herein, there is provided an expandable intervertebral fusion implant, comprising an inferior component, including a first horizontal member, a first vertical member connected to the first horizontal member, and a first outward facing surface, a superior component hingedly connected to the inferior component, the superior component including a second horizontal member, a second vertical member connected to the second horizontal member, and a second outward facing surface directed away from the first outward facing surface, a first shell hingedly connected to the inferior component, and a first wedging component slidingly arranged between the first shell and the first outward facing surface.

In some embodiments, the first vertical member is arranged at a proximal end of the inferior component, and the first shell is hingedly connected to the inferior component at the proximal end of the inferior component. In some embodiments, the first vertical member comprises a first plurality of teeth, the second vertical member comprises a second plurality of teeth, and the second plurality of teeth are operatively arranged to engage the first plurality of teeth to lock the superior component with respect to the inferior component. In some embodiments, when the first wedging component is displaced in a first direction with respect to the first outer surface, the first shell is displaced away from the first outer surface. In some embodiments, the expandable intervertebral fusion implant further comprises a first screw engaged with the first wedging component, wherein when the first screw is rotated in a first rotational direction the first wedging component is displaced in the first direction. In some embodiments, the expandable intervertebral fusion implant further comprises a second shell hingedly connected to the superior component, and a second wedging component slidingly arranged between the second shell and the second outward facing surface. In some embodiments, the expandable intervertebral fusion implant further comprises a second shell hingedly connected to the inferior component, and a second wedging component slidingly arranged between the second shell and the first outward facing surface. In some embodiments, when the first wedging component is displaced in a first direction with respect to the first outer surface, the first shell is displaced away from the first outer surface, and when the second wedging component is displaced in a second direction with respect to the first outer surface, opposite the first direction, the second shell is displaced away from the first outer surface.

According to aspects illustrated herein, there is provided an expandable intervertebral fusion implant, comprising an inferior component, including a first horizontal member including a first proximal end and a first distal end, a first vertical member connected to the first proximal end, a second vertical member connected to the first distal end, and a first outward facing surface, a superior component, including a second horizontal member including a second proximal end and a second distal end, a third vertical member connected to the second proximal end, a fourth vertical member connected to the second distal end, the fourth vertical member hingedly connected to the second vertical member, and a second outward facing surface directed away from the first outward facing surface, a first shell hingedly connected to the inferior component, and a first wedging component slidingly arranged between the first shell and the first outward facing surface.

In some embodiments, the first shell is hingedly connected to the inferior component at the first proximal end. In some embodiments, the first vertical member comprises a first plurality of teeth, the third vertical member comprises a second plurality of teeth, and the second plurality of teeth are operatively arranged to engage the first plurality of teeth to lock the superior component with respect to the inferior component. In some embodiments, when the first wedging component is displaced in a first direction with respect to the first outer surface, the first shell is displaced away from the first outer surface. In some embodiments, the expandable intervertebral fusion implant further comprises a first screw engaged with the first wedging component, wherein when the first screw is rotated in a first rotational direction the first wedging component is displaced in the first direction. In some embodiments, the expandable intervertebral fusion implant further comprises a second shell hingedly connected to the superior component, and a second wedging component slidingly arranged between the second shell and the second outward facing surface. In some embodiments, the expandable intervertebral fusion implant further comprises a second shell hingedly connected to the inferior component, and a second wedging component slidingly arranged between the second shell and the first outward facing surface. In some embodiments, when the first wedging component is displaced in a first direction with respect to the first outer surface, the first shell is displaced away from the first outer surface, and when the second wedging component is displaced in a second direction with respect to the first outer surface, opposite the first direction, the second shell is displaced away from the first outer surface.

According to aspects illustrated herein, there is provided an expandable intervertebral fusion implant, comprising an inferior component, including a first horizontal member including a first proximal end and a first distal end, a first vertical member connected to the first proximal end and comprising a first plurality of teeth, a first outward facing surface, a superior component, including a second horizontal member including a second proximal end and a second distal end, the second distal end being pivotably connected to the first distal end, a second vertical member connected to the second proximal end and including a second plurality of teeth, the second plurality of teeth operatively arranged to engage the first plurality of teeth to lock the superior component with respect to the inferior component, and a second outward facing surface directed away from the first outward facing surface, a first shell hingedly connected to the inferior component, and a first wedging component slidingly arranged between the first shell and the first outward facing surface.

In some embodiments, the first shell is hingedly connected to the inferior component at the first proximal end. In some embodiments, when the first wedging component is displaced in a first direction with respect to the first outer surface, the first shell is displaced away from the first outer surface. In some embodiments, the expandable intervertebral fusion implant further comprises a second shell hingedly connected to the superior component, and a second wedging component slidingly arranged between the second shell and the second outward facing surface, wherein as the second wedging component is displaced in the first direction the second shell is displaced away from the second outer surface.

These and other objects, features, and advantages of the present disclosure will become readily apparent upon a review of the following detailed description of the disclosure, in view of the drawings and appended claims.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

At the outset, it should be appreciated that like drawing numbers on different drawing views identify identical, or functionally similar, structural elements. It is to be understood that the claims are not limited to the disclosed aspects.

Furthermore, it is understood that this disclosure is not limited to the particular methodology, materials and modifications described and as such may, of course, vary. It is also understood that the terminology used herein is for the purpose of describing particular aspects only, and is not intended to limit the scope of the claims.

Unless defined otherwise, all technical and scientific terms used herein have the same meaning as commonly understood to one of ordinary skill in the art to which this disclosure pertains. It should be understood that any methods, devices or materials similar or equivalent to those described herein can be used in the practice or testing of the example embodiments. The assembly of the present disclosure could be driven by hydraulics, electronics, pneumatics, and/or springs.

It should be appreciated that the term "substantially" is synonymous with terms such as "nearly," "very nearly," "about," "approximately," "around," "bordering on," "close to," "essentially," "in the neighborhood of," "in the vicinity of," etc., and such terms may be used interchangeably as appearing in the specification and claims. It should be appreciated that the term "proximate" is synonymous with terms such as "nearby," "close," "adjacent," "neighboring," "immediate," "adjoining," etc., and such terms may be used interchangeably as appearing in the specification and claims. The term "approximately" is intended to mean values within ten percent of the specified value.

By "non-rotatably connected" elements, we mean that: the elements are connected so that whenever one of the elements rotate, all the elements rotate; and, relative rotation between the elements is not possible. Radial and/or axial movement of non-rotatably connected elements with respect to each other is possible, but not required. By "rotatably connected" elements, we mean that: the elements are rotatable with respect to each other; and, whenever one element is displaced radially and/or axially, all the elements are displaced radially and/or axially.

Adverting now to the figures, and as described previously, FIGS. 1-6 depict various parts and sections of spinal anatomy.

Figure 1:
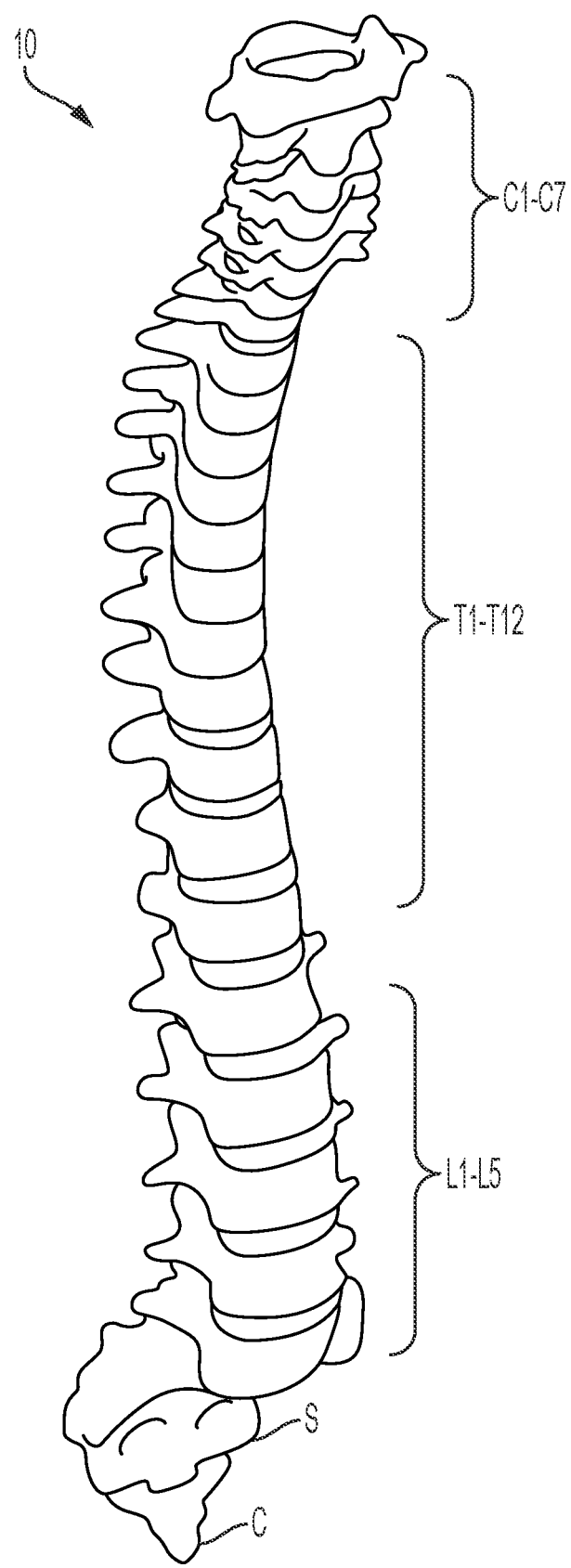
FIG. 1 is an anterior perspective view of a spinal column.
Figure 2:
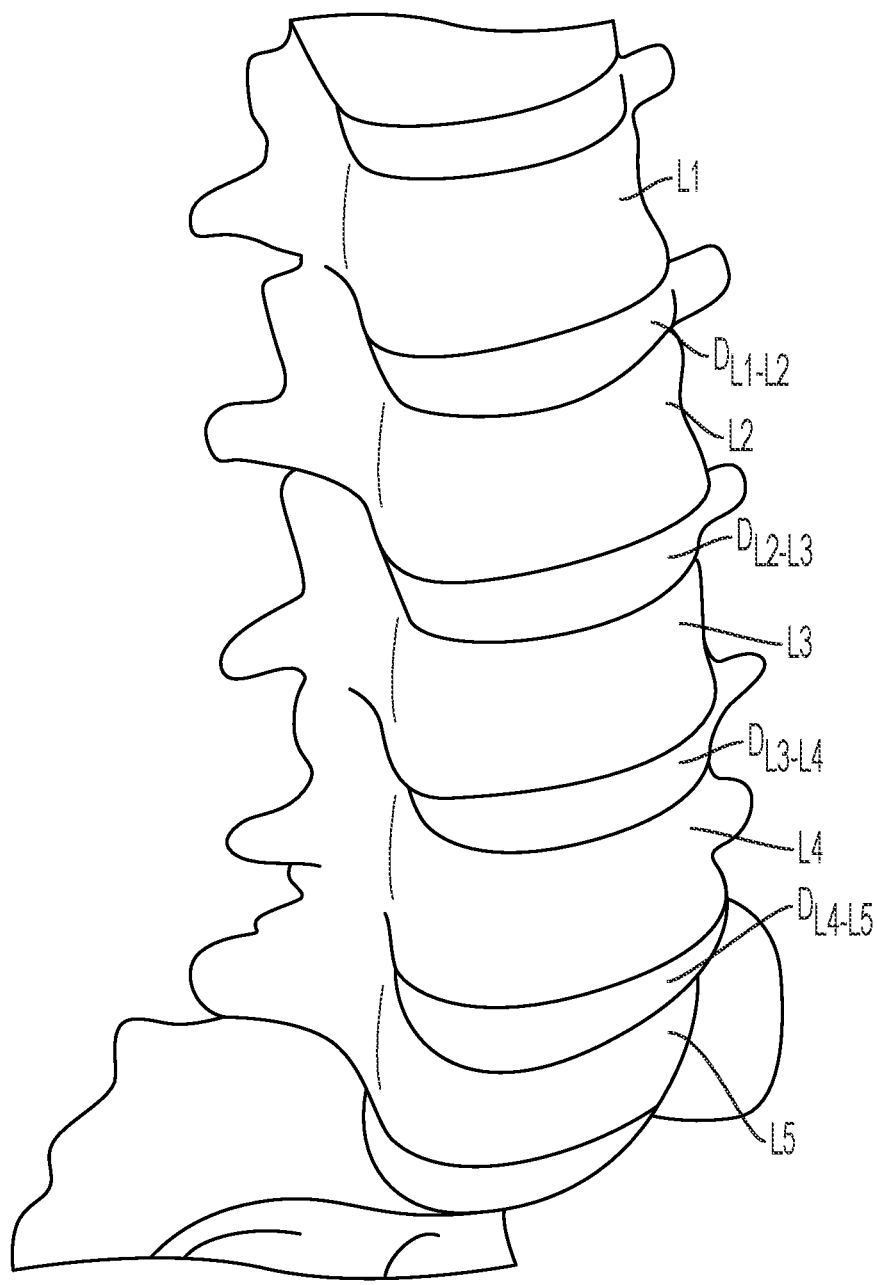
FIG. 2 is an anterior perspective view of the lumbar section of the spinal column shown in FIG. 1.
Figure 3:
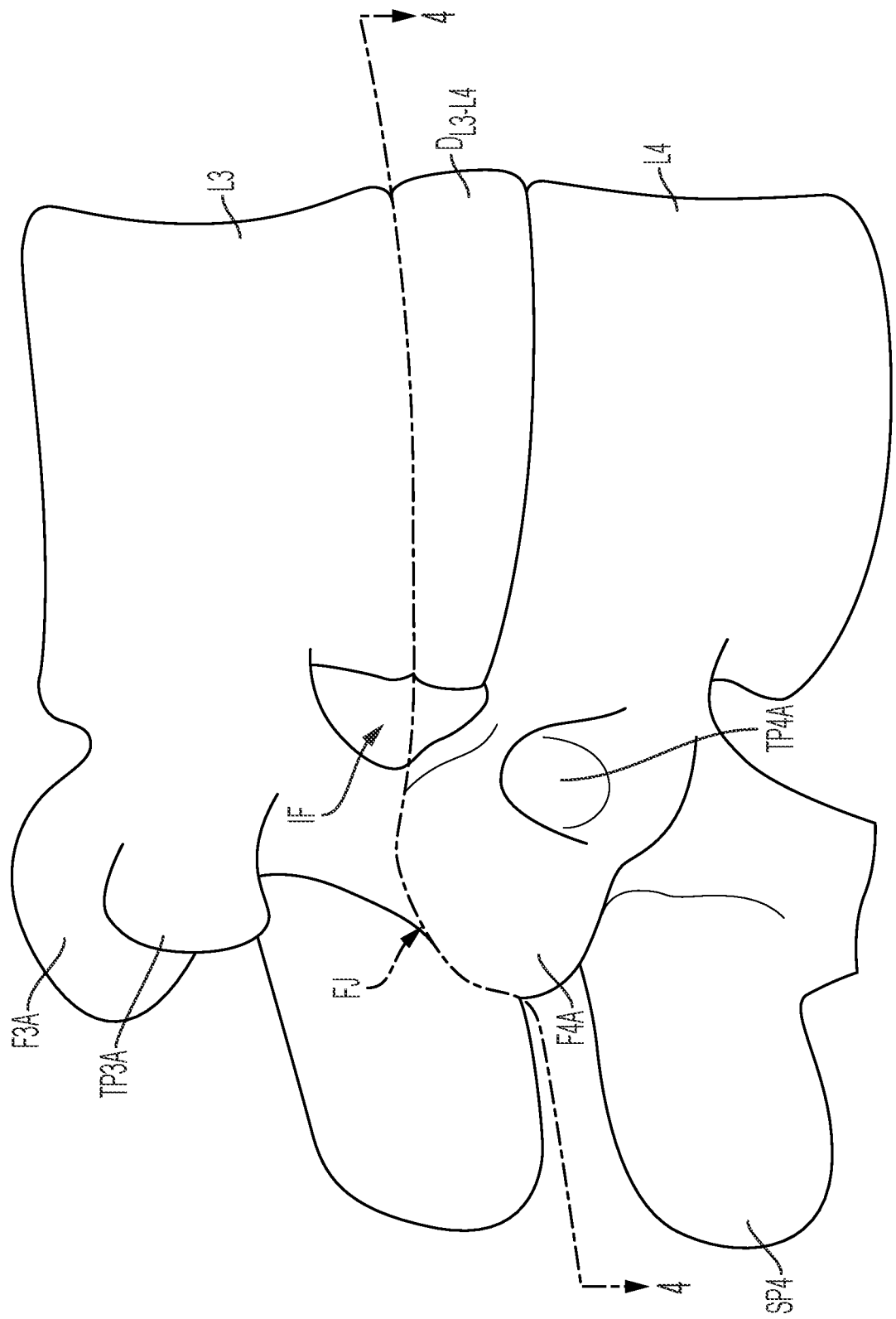
FIG. 3 is a lateral perspective view of two vertebrae, a disc, and related spinal anatomy.
Figure 4:
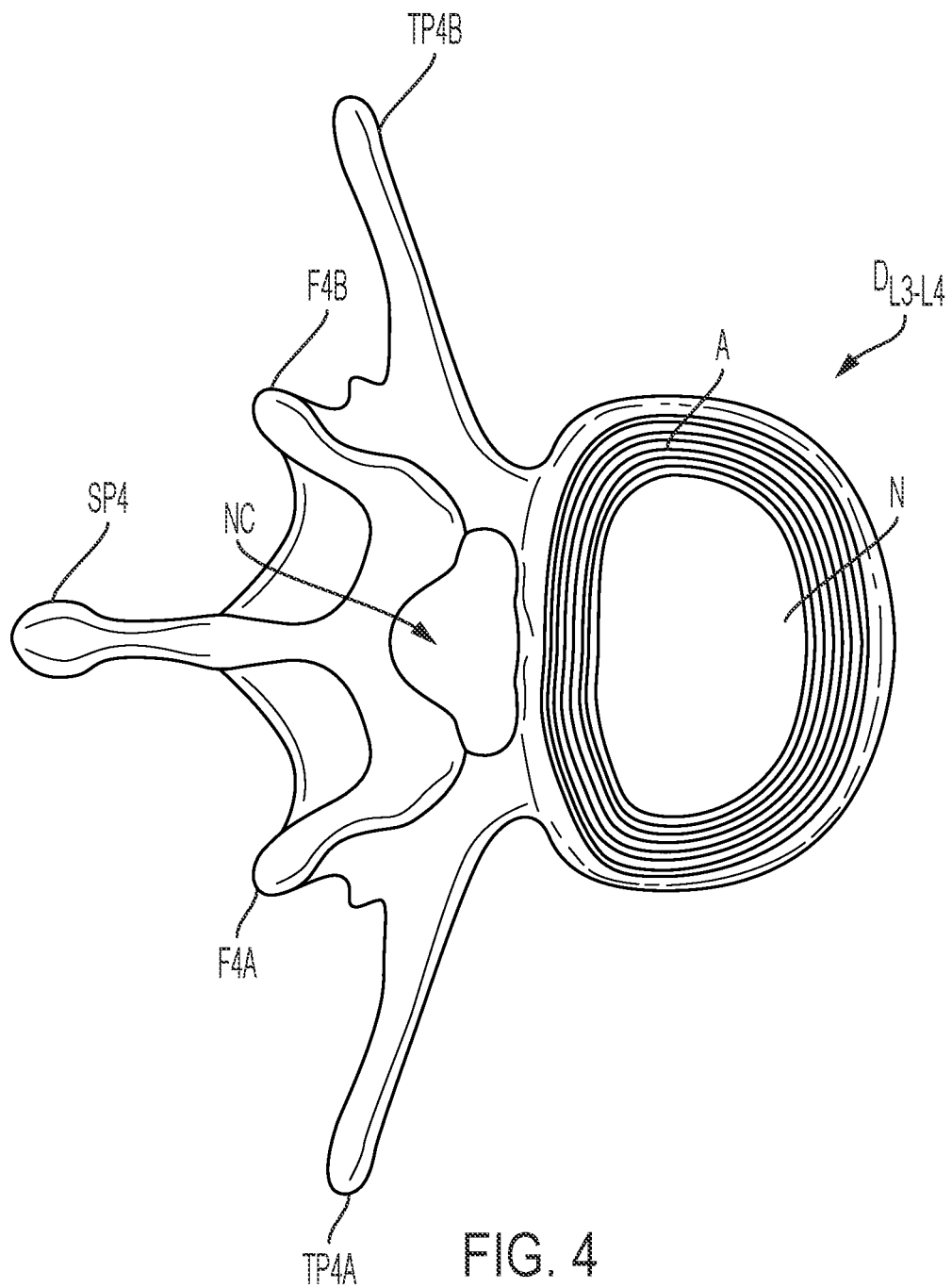
FIG. 4 is a top view of a section of the spinal column, taken generally along line 4-4 in FIG. 3.
Figure 5:
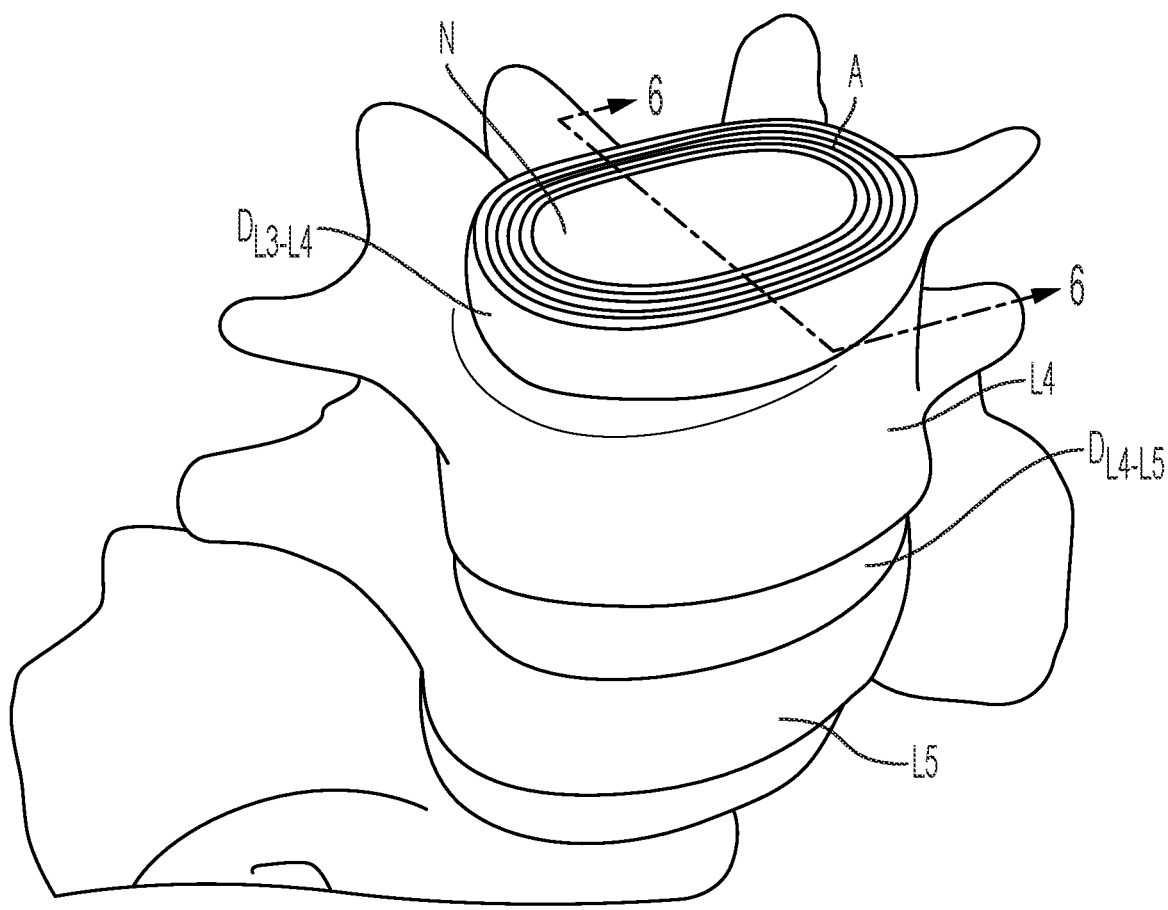
FIG. 5 is an enlarged anterior perspective view of the spinal column shown in FIG. 2, except with the top vertebra and all other structure above the top vertebra removed.
Figure 6:
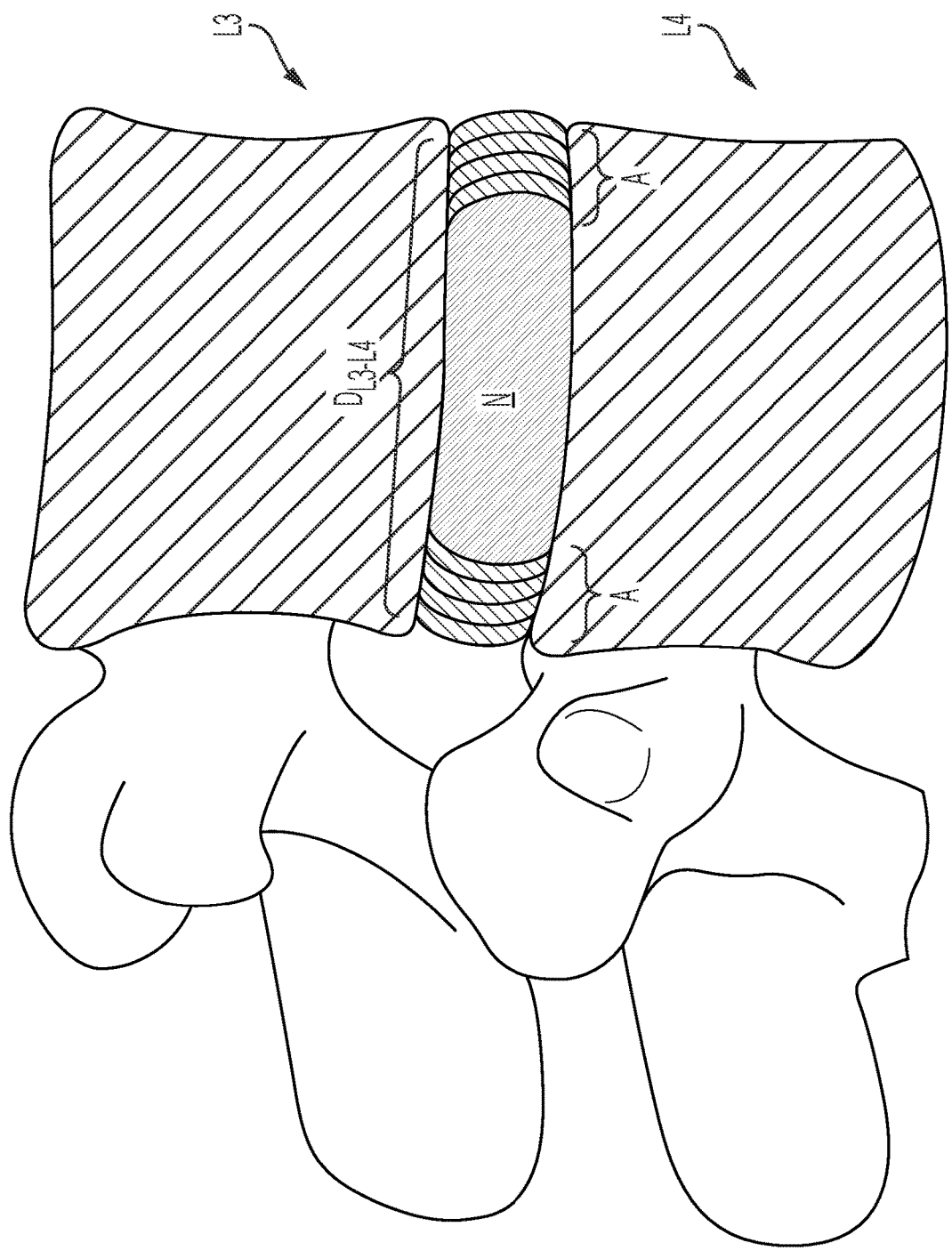
FIG. 6 is a partial cross-sectional view of the top and bottom vertebrae and disc, taken generally along line 6-6 in FIG. 5.
Figure 7:
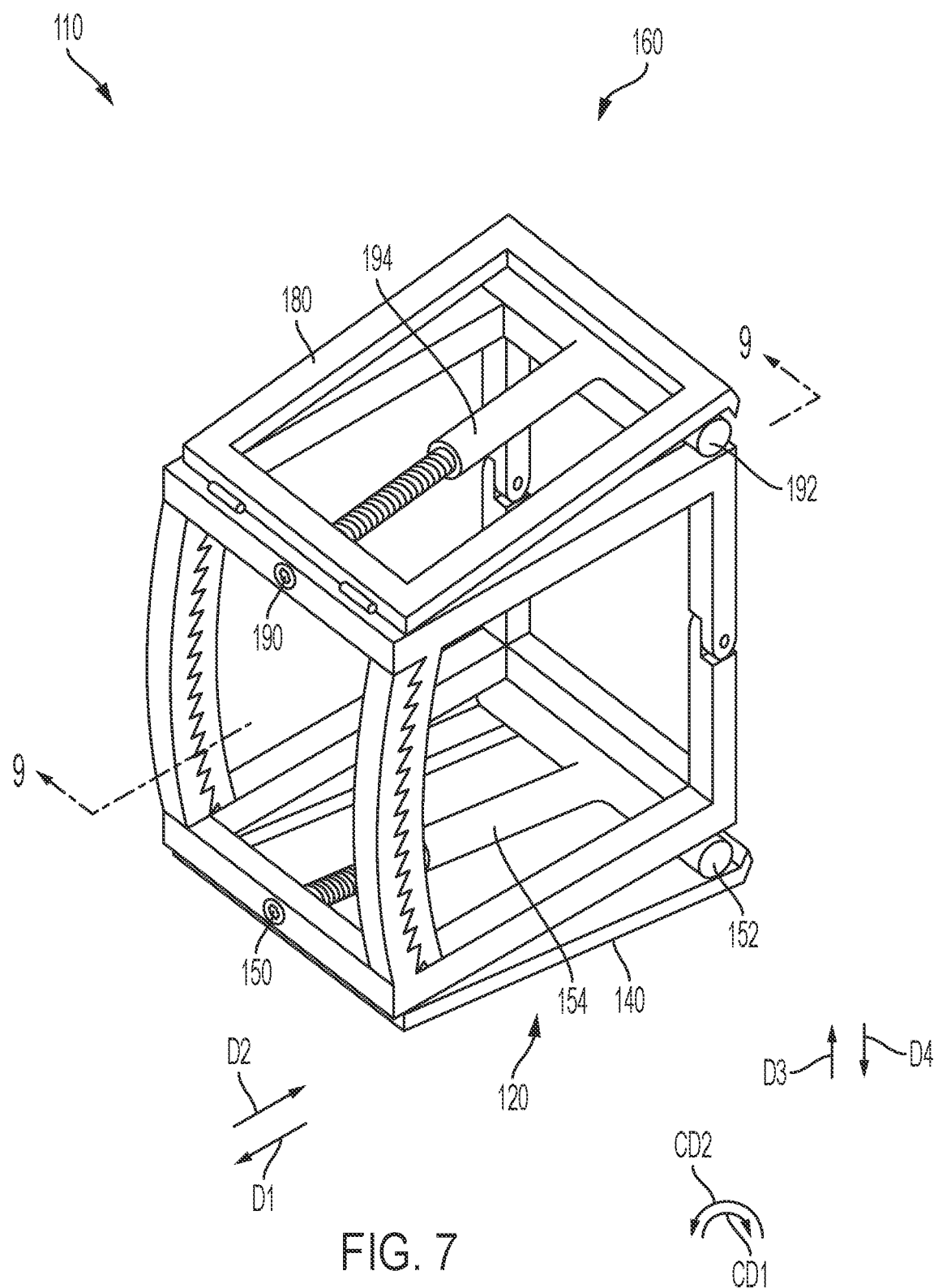
FIG. 7 is a front perspective view of an expandable intervertebral fusion implant, in a collapsed state.
Figure 8:
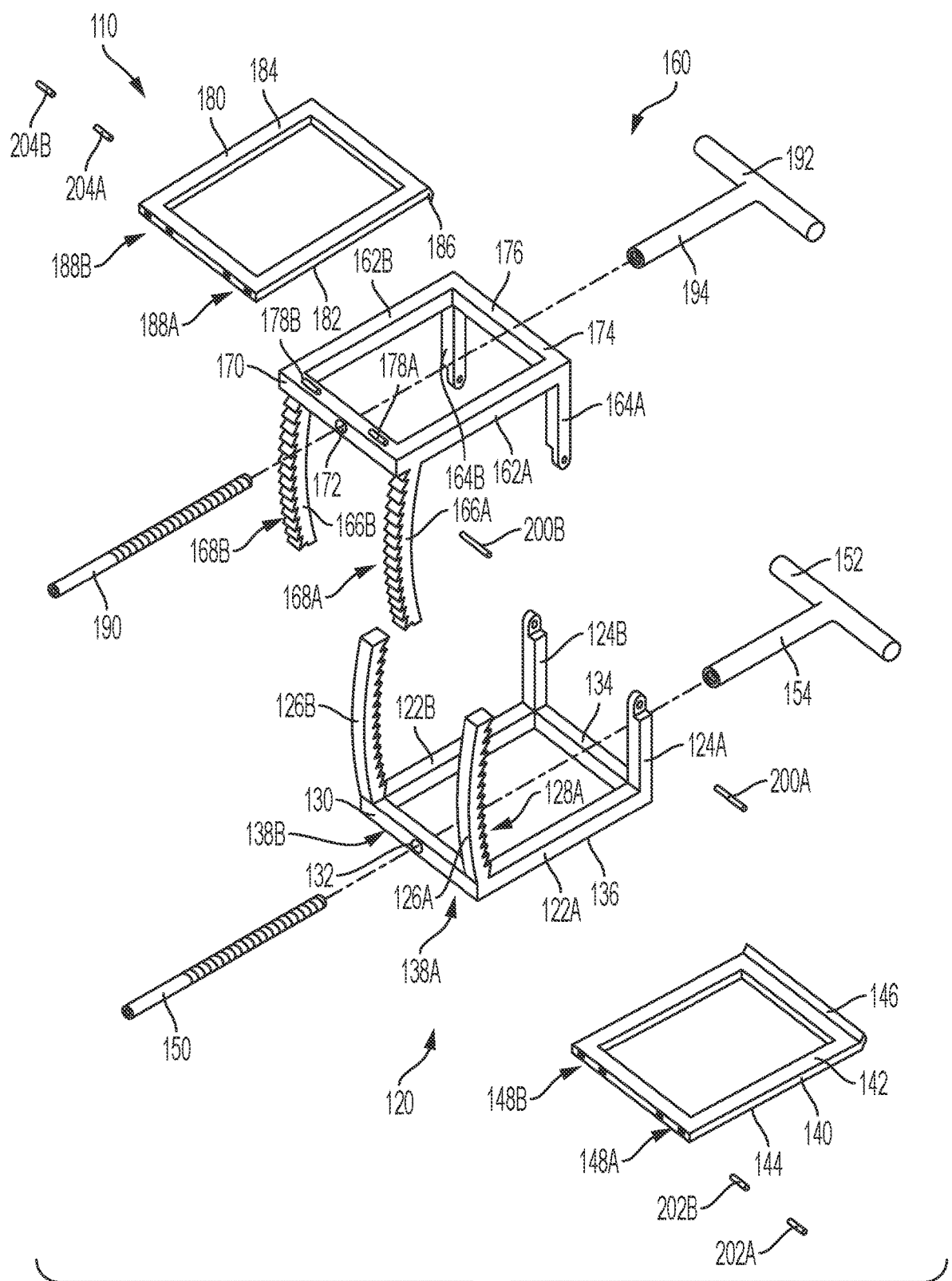
FIG. 8 is an exploded perspective view of the expandable intervertebral fusion implant shown in FIG. 7.
Figure 9A:
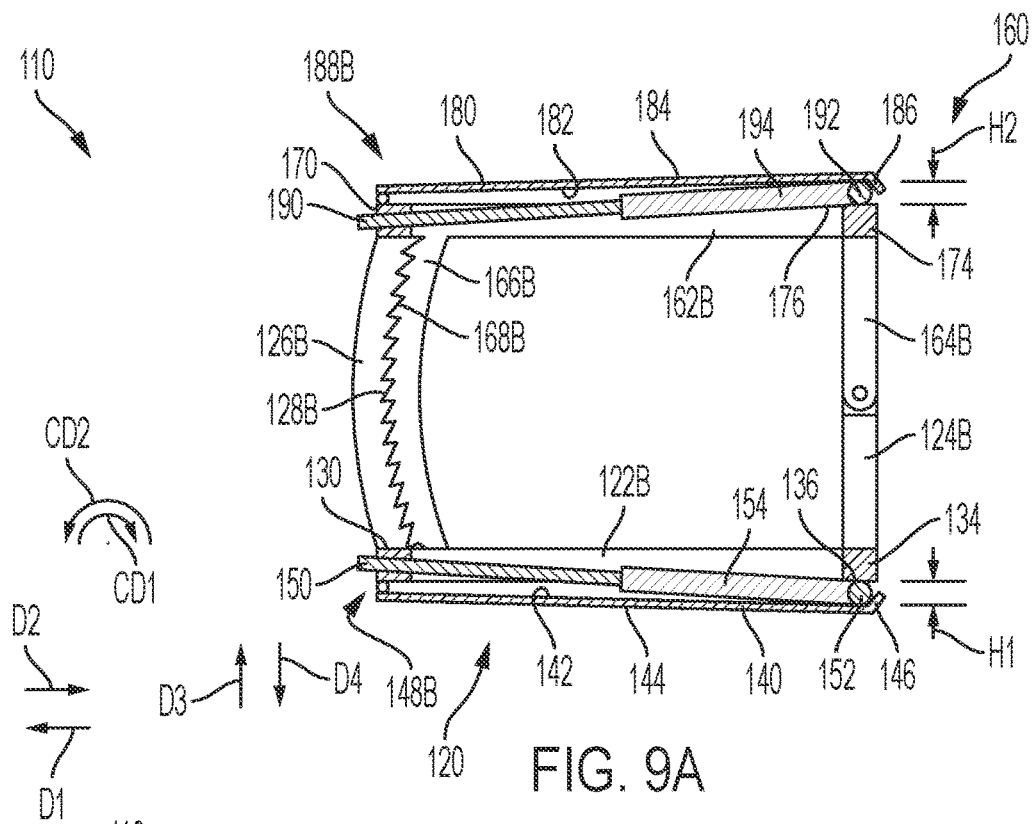
FIG. 9A is a cross-sectional view of the expandable intervertebral fusion implant taken generally along line 9-9 in FIG. 7, in the collapsed state.
Figure 9B:
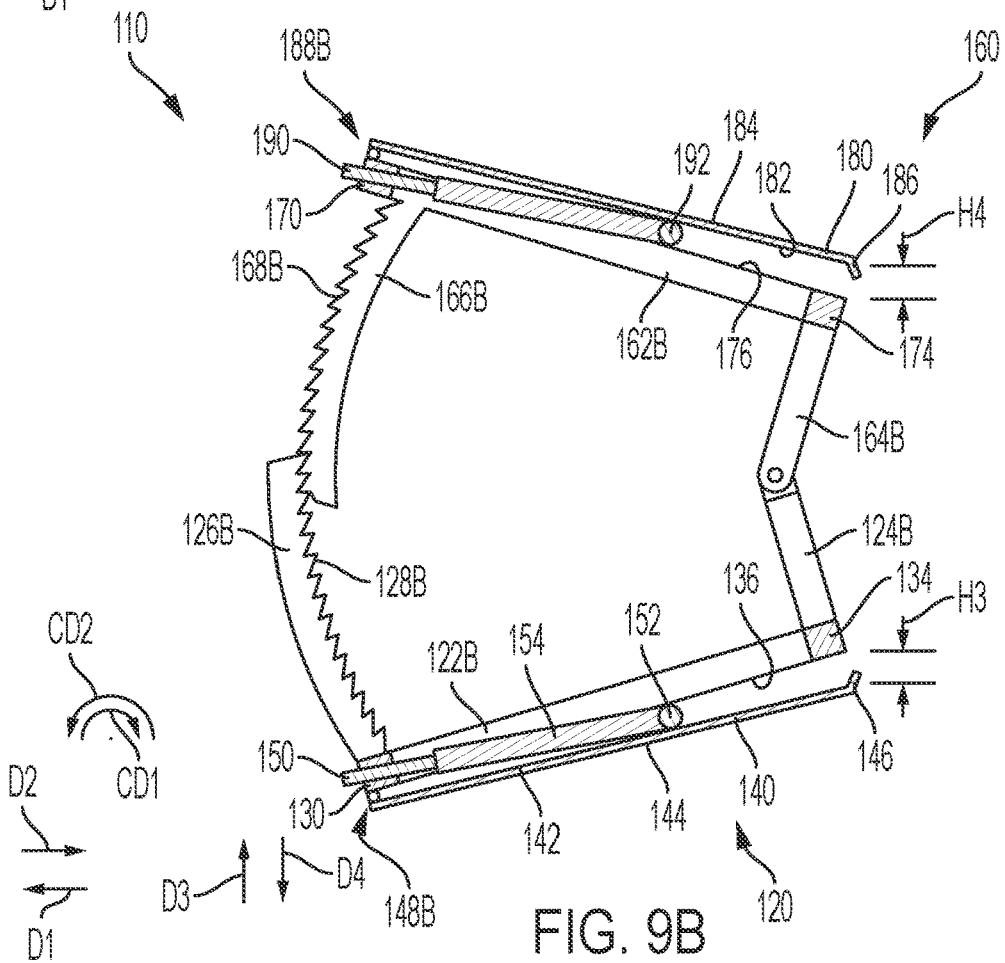
FIG. 9B is a cross-sectional view of the expandable intervertebral fusion implant taken generally along line 9-9 in FIG. 7, in an expanded state.

FIG. 7 is a front perspective view of expandable intervertebral fusion implant 110, in a collapsed state. FIG. 8 is an exploded perspective view of expandable intervertebral fusion implant 110. FIG. 9A is a cross-sectional view of expandable intervertebral fusion implant 110 taken generally along line 9-9 in FIG. 7, in the collapsed state. FIG. 9B is a cross-sectional view of expandable intervertebral fusion implant 110 taken generally along line 9-9 in FIG. 7, in an expanded state. Expandable intervertebral fusion implant 110 generally comprises inferior component 120, superior component 160, at least one shell, for example, shell 140 and/or shell 180, and at least one expansion mechanism, for example, screw 150 and wedging component 152, and/or screw 190 and wedging component 192. The following description should be read in view of FIGS. 7-9B.

Inferior component 120 comprises horizontal members 122A-B, vertical members 124A-B, vertical members 126A-B, horizontal member 130, and horizontal member 134. Inferior component 120 comprises exterior surface 136. In some embodiments, surface 136 is formed by horizontal members 122A-B, 130, and 134 and is operatively arranged to engage an expansion mechanism, as will be described in greater detail below.

Vertical members 124A-B are connected and extend generally in direction D3 with respect to horizontal member 134 and/or horizontal members 122A-B. In some embodiments, vertical members 124A-B are perpendicular to surface 136. In some embodiments, vertical members 124A-B are fixedly secured to horizontal member 134 and/or horizontal members 122A-B. Vertical members 124A-B are operatively arranged to hingedly or pivotably connect inferior component 120 to superior component 160. In some embodiments, vertical members 124A-B are pivotably connected to vertical members 164A-B via pins 200A-B.

Vertical members 126A-B are connected and extend generally in direction D3 with respect to horizontal member 130 and/or horizontal members 122A-B. In some embodiments, vertical members 126A-B are perpendicular to surface 136. In some embodiments, vertical members 126A-B are fixedly secured to horizontal member 130 and/or horizontal members 122A-B. Vertical members 126A-B are operatively arranged to engage vertical members 166A-B, respectively, to lock superior component 160 with respect to inferior component 120. In some embodiments, vertical members 126A-B comprise plurality of teeth 128A-B. Teeth 128A-B are operatively arranged to engage teeth 168A-B such that superior component 160 is capable of displacing in direction D3 (or circumferential direction CD1) with respect to inferior component 120, but not in direction D4 (or circumferential direction CD2) with respect to inferior component 120.

Horizontal members 122A-B, 130, and 134 are arranged such that an aperture is formed therebetween. Such aperture allows bone material injected into expandable intervertebral fusion implant 110 to fuse with an adjacent vertebra. It should be appreciated that, while horizontal members 122A-B, 130, and 134 form a rectangular or square-shaped opening, the aperture or opening within the horizontal members of inferior component 120 may comprise any suitable geometry (e.g., triangular, circular, ovular, ellipsoidal, trapezoidal, etc.). In some embodiments, horizontal member 130 comprises hole 132. Hole 132 is operatively arranged to engage screw 150. In some embodiments, inferior component 120 further comprises one or more hinge components, for example, hinge components 138A-B. In some embodiments, hinge components 138A-B are connected to surface 136. In some embodiments, "hinge component" refers to knuckles of a hinge.

The expansion mechanism of inferior component 120 generally comprises shell 140, screw 150, and wedging component 152. Shell 140 is hingedly connected to at least one member of inferior component 120. In some embodiments, shell 140 is hingedly connected to surface 136. In some embodiments, shell 140 is hingedly connected to member 130. Shell 140 comprises surface 142, surface 144, and flange 146. Shell 140 is connected to inferior component 120 such that surface 142 generally faces toward surface 136 and surface 144 generally faces away from surface 136. Surface 142 is operatively arranged to engage with wedging component 152 and surface 144 is operatively arranged to engage an adjacent vertebra. Flange 146 extends from surface 142 in direction D3 and is operatively arranged to engage wedging component 152. Flange 146 prevents wedging component 152 from displacing in direction D2 (i.e., extending beyond surfaces 136 and 142). In some embodiments, shell 140 comprises an aperture to allow bone material injected into expandable intervertebral fusion implant 110 to fuse with an adjacent vertebra. In some embodiments, shell 140 further comprises one or more hinge components, for example, hinge components 148A-B, that connect to one or more hinge components of inferior component 120, for example, hinge components 138A-B, via one or more pins, for example, pins 202A-B. As previously described, hinge components 138A-B and 148A-B are the alternating knuckles of the hinge and are secured together via pins 202A-B. It should be appreciated that other forms of hinged or pivotable connection may be used to hingedly or pivotably connect shell 140 to inferior component 120, for example, a living hinge, a ball and socket joint, etc.

Screw 150 is operatively arranged to rotatably connect to inferior component 120. Specifically, screw 150 comprises a proximal end including a head that is rotatably connected to inferior component 120 and a distal end including threading. In some embodiments, and as shown, screw 150 is rotatably engaged with hole 132. The threading of screw 150 is threadably engaged with wedging component 152. Specifically, wedging component 152 comprises sleeve 154 that is threadably connected to screw 150. As screw 150 is rotated in a first rotational direction, sleeve 154, and thus wedging component 152, is displaced in direction D1. As screw 150 is rotated in a second rotational direction, opposite the first rotational direction, sleeve 154, and thus wedging component 152, is displaced in direction D2.

Wedging component 152 is operatively arranged to be displaced in direction D1 along surfaces 136 and 142 to displace shell 140 in direction D4 (or circumferential direction CD1) thus expanding expandable intervertebral fusion implant 110, and direction D2 along surfaces 136 and 142 to displace shell 140 in direction D3 (or circumferential direction CD2) thus contracting expandable intervertebral fusion implant 110. It should be appreciated that while wedging component 152 is generally shown as a cylindrical member, wedging component 152 may comprise any geometry suitable for displacing shell 140 with respect to inferior component 120, for example, triangular prism, rectangular prism, square prism, wedge-shaped or wedge prism, ovular prism, etc. Wedging component 152 allows the distal end of expandable intervertebral fusion implant 110 to be expanded after (or before) insertion into a disc space. Thus, expandable intervertebral fusion implant 110 can be inserted distal end (i.e., horizontal member 134 and 174) first into a disc space between two vertebrae, proximal end (i.e., horizontal members 130 and 170) can be expanded to the desired height, and distal end can then be expanded by rotating screw 150.

Superior component 160 comprises horizontal members 162A-B, vertical members 164A-B, vertical members 166A-B, horizontal member 170, and horizontal member 174. Superior component 160 comprises exterior surface 176. In some embodiments, surface 176 is formed by horizontal members 162A-B, 170, and 174 and is operatively arranged to engage an expansion mechanism, as will be described in greater detail below.

Vertical members 164A-B are connected and extend generally in direction D4 with respect to horizontal member 174 and/or horizontal members 162A-B. In some embodiments, vertical members 164A-B are perpendicular to surface 176. In some embodiments, vertical members 164A-B are fixedly secured to horizontal member 174 and/or horizontal members 162A-B. Vertical members 164A-B are operatively arranged to hingedly or pivotably connect superior component 160 to inferior component 120. In some embodiments, vertical members 164A-B are pivotably connected to vertical members 124A-B via pins 200A-B.

Vertical members 166A-B are connected and extend generally in direction D4 with respect to horizontal members 162A-B. In some embodiments, vertical members 166A-B are perpendicular to surface 176. In some embodiments, vertical members 166A-B are fixedly secured to horizontal members 162A-B, respectively. Vertical members 166A-B are operatively arranged to engage vertical members 126A-B, respectively, to lock superior component 160 with respect to inferior component 120. In some embodiments, vertical members 166A-B comprise plurality of teeth 168A-B. Teeth 168A-B are operatively arranged to engage teeth 128A-B such that superior component 160 is capable of displacing in direction D3 (or circumferential direction CD1) with respect to inferior component 120, but not in direction D4 (or circumferential direction CD2) with respect to inferior component 120.

Horizontal members 162A-B, 170, and 174 are arranged such that an aperture is formed therebetween. Such aperture allows bone material injected into expandable intervertebral fusion implant 110 to fuse with an adjacent vertebra. It should be appreciated that, while horizontal members 162A-B, 170, and 174 form a rectangular or square-shaped opening, the aperture or opening within the horizontal members of superior component 160 may comprise any suitable geometry (e.g., triangular, circular, ovular, ellipsoidal, trapezoidal, etc.). In some embodiments, horizontal member 170 comprises hole 172. Hole 172 is operatively arranged to engage screw 190. In some embodiments, superior component 160 further comprises one or more hinge components, for example, hinge components 178A-B. In some embodiments, hinge components 178A-B are connected to surface 176.

The expansion mechanism of superior component 160 generally comprises shell 180, screw 190, and wedging component 192. Shell 180 is hingedly connected to at least one member of superior component 160. In some embodiments, shell 180 is hingedly connected to surface 176. In some embodiments, shell 180 is hingedly connected to member 170. Shell 180 comprises surface 182, surface 184, and flange 186. Shell 180 is connected to superior component 160 such that surface 182 generally faces toward surface 176 and surface 184 generally faces away from surface 176. Surface 182 is operatively arranged to engage with wedging component 192 and surface 184 is operatively arranged to engage an adjacent vertebra. Flange 186 extends from surface 182 in direction D4 and is operatively arranged to engage wedging component 192. Flange 186 prevents wedging component 192 from displacing in direction D2 (i.e., extending beyond surfaces 176 and 182). In some embodiments, shell 180 comprises an aperture to allow bone material injected into expandable intervertebral fusion implant 110 to fuse with an adjacent vertebra. In some embodiments, shell 180 further comprises one or more hinge components, for example, hinge components 188A-B, that connect to one or more hinge components of superior component 160, for example, hinge components 178A-B, via one or more pins, for example, pins 204A-B. As previously described, hinge components 178A-B and 188A-B are the alternating knuckles of the hinge and are secured together via pins 204A-B. It should be appreciated that other forms of hinged or pivotable connection may be used to hingedly or pivotably connect shell 190 to superior component 160, for example, a living hinge, a ball and socket joint, etc.

Screw 190 is operatively arranged to rotatably connect to superior component 160. Specifically, screw 190 comprises a proximal end including a head that is rotatably connected to superior component 160 and a distal end including threading. In some embodiments, and as shown, screw 190 is rotatably engaged with hole 172. The threading of screw 190 is threadably engaged with wedging component 192. Specifically, wedging component 192 comprises sleeve 194 that is threadably connected to screw 190. As screw 190 is rotated in a first rotational direction, sleeve 194, and thus wedging component 192, is displaced in direction D1. As screw 190 is rotated in a second rotational direction, opposite the first rotational direction, sleeve 194, and thus wedging component 192, is displaced in direction D2.

Wedging component 192 is operatively arranged to be displaced in direction D1 along surfaces 176 and 182 to displace shell 180 in direction D3 (or circumferential direction CD2) thus expanding expandable intervertebral fusion implant 110, and direction D2 along surfaces 176 and 182 to displace shell 180 in direction D4 (or circumferential direction CD1) thus contracting expandable intervertebral fusion implant 110. It should be appreciated that while wedging component 192 is generally shown as a cylindrical member, wedging component 192 may comprise any geometry suitable for displacing shell 180 with respect to superior component 160, for example, triangular prism, rectangular prism, square prism, wedge-shaped or wedge prism, ovular prism, etc. Wedging component 192 allows the distal end of expandable intervertebral fusion implant 110 to be expanded after (or before) insertion into a disc space. Thus, expandable intervertebral fusion implant 110 can be inserted distal end (i.e., horizontal member 134 and 174) first into a disc space between two vertebrae, proximal end (i.e., horizontal members 130 and 170) can be expanded to the desired height, and distal end can then be expanded by rotating screw 190.

In the fully collapsed state, as best shown in FIGS. 7 and 9A, the distal ends of vertical members 126A-B are engaged with and/or abut against horizontal member 170. Vertical members 124A-B are generally aligned with vertical members 164A-B. Wedging component 152 is arranged at the distal end of expandable intervertebral fusion implant 110 (i.e., proximate member 134) such that surface 142 is spaced apart from surface 136 by height H1. In some embodiments, height H1 is the height of wedging component 152. Wedging component 192 is arranged at the distal end of expandable intervertebral fusion implant 110 (i.e., proximate member 174) such that surface 182 is spaced apart from surface 176 by height H2. In some embodiments, height H2 is the height of wedging component 192. In some embodiments, height H2 is equal to height H1. In some embodiments, height H2 is not equal to height H1.

To expand expandable intervertebral fusion implant 110, an expansion mechanism is used to expand the proximal end (i.e., horizontal members 130 and 170) thereof. An example of an expansion mechanism is disclosed in U.S. Pat. No. 10,470,895 (Suddaby), which patent is incorporated herein by reference in its entirety. Furthermore, the distal end (i.e., horizontal members 134 and 174) is then expanded by turning at least one of screws 150 and 190. As previously described, rotating screw 150 in a first rotational direction causes wedging component 152 to displace in direction D1 thereby displacing shell 140 in direction D4 (or circumferential direction CD1), thus expanding the distal end of expandable intervertebral fusion implant 110. Similarly, rotating screw 190 in a first rotational direction causes wedging component 192 to displace in direction D1 thereby displacing shell 180 in direction D3 (or circumferential direction CD2).

FIG. 9B shows expandable intervertebral fusion implant 110 in an expanded state. As shown, proximal end (i.e., left side or members 130 and 170) has been expanded. Additionally, wedging component 152 has been displaced in direction D1 forcing shell 140 in direction D4 (or circumferential direction CD1) such that surface 142 is spaced apart from surface 136 by height H3. Height H3 is greater than height H1. Wedging component 192 has been displaced in direction D1 forcing shell 180 in direction D3 (or circumferential direction CD2) such that surface 182 is spaced apart from surface 176 by height H4. Height H4 is greater than height H2. In some embodiments, height H4 is equal to height H3. In some embodiments, height H4 is not equal to height H3. To contract expandable intervertebral fusion implant 110, screw 150 is rotated in a second rotational direction, opposite the first rotational direction, which displaces wedging component 152 in direction D2, allowing shell 140 to collapse in direction D3 (or circumferential direction CD2). Screw is rotated in a second rotational direction, opposite the first rotational direction, which displaces wedging component 192 in direction D2, allowing shell 180 to collapse in direction D4 (or circumferential direction CD1). It should be appreciated that, in some embodiments, vertical members 126A-B and/or vertical members 166A-B are elastically displaceable. As such, to collapse the proximal end of expandable intervertebral fusion implant 110, vertical members 126A-B are displaced elastically such that teeth 128A-B disengage teeth 168A-B, at which point horizontal member 170 can be displaced in direction D4 with respect to horizontal member 130.

Figure 10A:
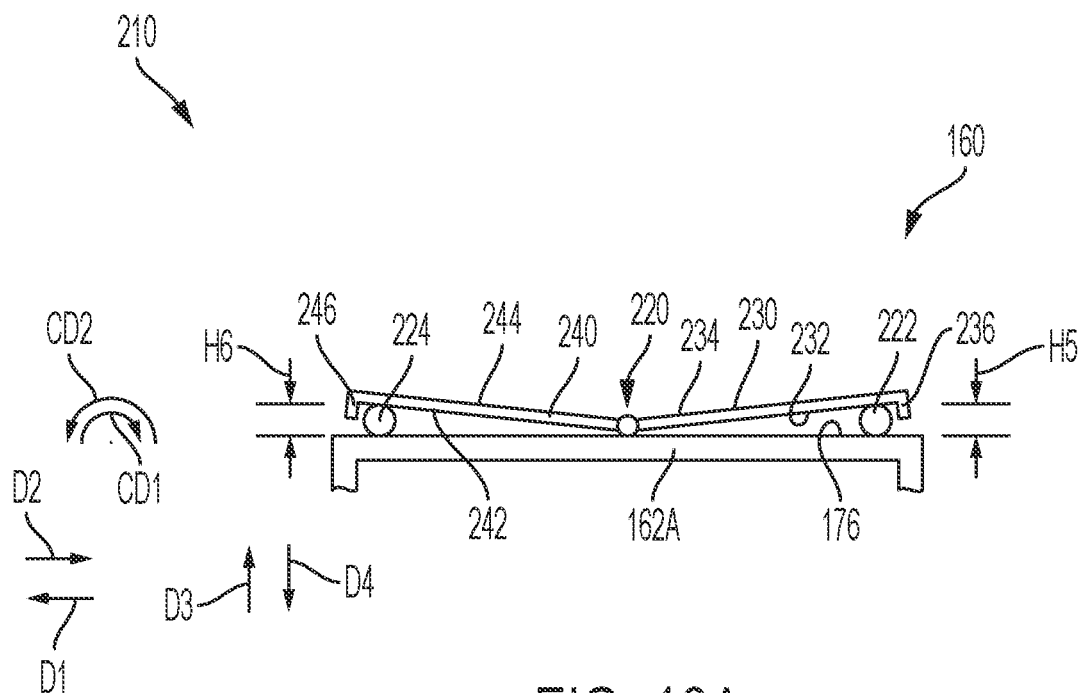
FIG. 10A is a partial side elevational view of an expandable intervertebral fusion implant in a collapsed state.
Figure 10B:
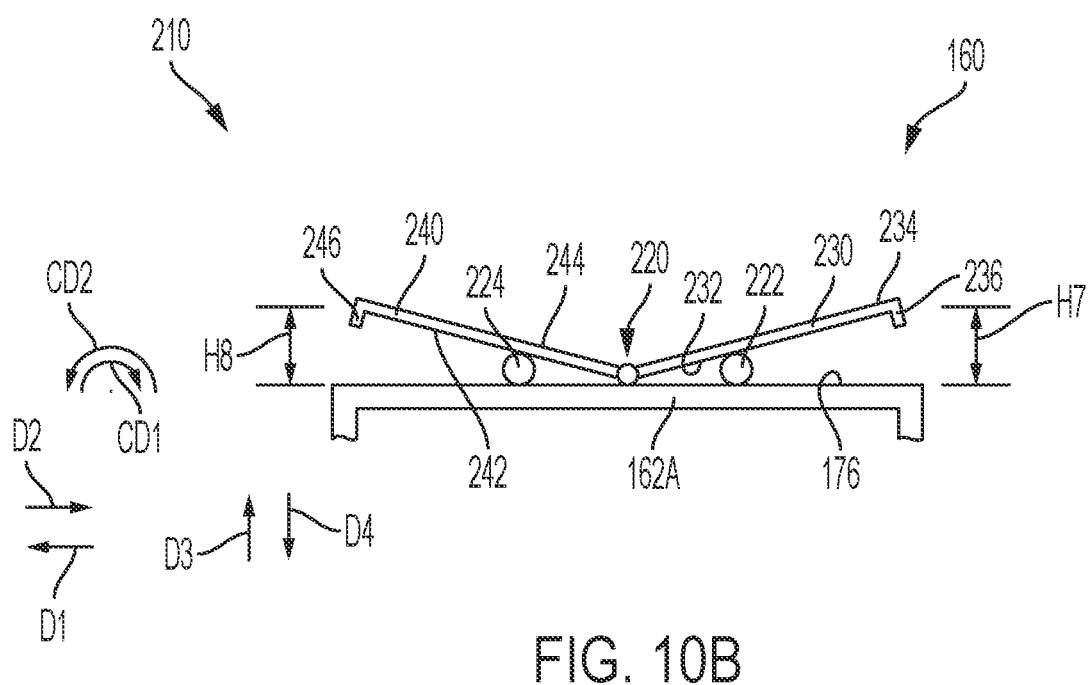
FIG. 10B is a partial side elevational view of the expandable intervertebral fusion implant shown in FIG. 10A, in an expanded state; and, FIG. 11 is an anterior perspective view of a spinal column including the expandable intervertebral fusion implant shown in FIG. 7, in an expanded state.

FIG. 10A is a partial side elevational view of expandable intervertebral fusion implant 210 in a collapsed state. FIG. 10B is a partial side elevational view of expandable intervertebral fusion implant 210, in an expanded state. Expandable intervertebral fusion implant 210 is substantially similar to expandable intervertebral fusion implant 210 but includes a different expansion mechanism. As shown, the expansion mechanism of expandable intervertebral fusion implant 210, and more specifically for superior component 160, comprises wedging component 222, wedging component 224, shell 230, and shell 240.

Shell 230 is hingedly connected to horizontal member 162A via hinge 220. Shell 230 comprises surface 232, surface 234, and flange 236. Shell 230 is connected to superior component 160 such that surface 232 generally faces toward surface 176 and surface 234 generally faces away from surface 176. Surface 232 is operatively arranged to engage with wedging component 222 and surface 234 is operatively arranged to engage an adjacent vertebra. Flange 236 extends from surface 232 in direction D4 and is operatively arranged to engage wedging component 222. Flange 236 prevents wedging component 222 from displacing in direction D2 (i.e., extending beyond surfaces 176 and 232). In some embodiments, shell 230 comprises an aperture to allow bone material injected into expandable intervertebral fusion implant 210 to fuse with an adjacent vertebra.

Wedging component 222 is operatively arranged to be displaced in direction D1 along surfaces 176 and 232 to displace shell 230 in direction D3 (or circumferential direction CD2) thus expanding expandable intervertebral fusion implant 210, and direction D2 along surfaces 176 and 232 to displace shell 230 in direction D4 (or circumferential direction CD1) thus contracting expandable intervertebral fusion implant 210. It should be appreciated that while wedging component 222 is generally shown having a circular cross-section, wedging component 222 may comprise any geometry suitable for displacing shell 230 with respect to superior component 160, for example, triangular prism, rectangular prism, square prism, wedge-shaped or wedge prism, ovular prism, etc. Wedging component 222 allows the distal end of expandable intervertebral fusion implant 210 to be expanded after (or before) insertion into a disc space. Any suitable means for displacing wedging component 222 in direction D1 and direction D2 may be used.

Shell 240 is hingedly connected to horizontal member 162A via hinge 220. Shell 240 comprises surface 242, surface 244, and flange 246. Shell 240 is connected to superior component 160 such that surface 242 generally faces toward surface 176 and surface 244 generally faces away from surface 176. Surface 242 is operatively arranged to engage with wedging component 224 and surface 244 is operatively arranged to engage an adjacent vertebra. Flange 246 extends from surface 242 in direction D4 and is operatively arranged to engage wedging component 224. Flange 246 prevents wedging component 224 from displacing in direction D1 (i.e., extending beyond surfaces 176 and 242). In some embodiments, shell 240 comprises an aperture to allow bone material injected into expandable intervertebral fusion implant 210 to fuse with an adjacent vertebra.

Wedging component 224 is operatively arranged to be displaced in direction D2 along surfaces 176 and 242 to displace shell 240 in direction D3 (or circumferential direction CD1) thus expanding expandable intervertebral fusion implant 210, and direction D1 along surfaces 176 and 242 to displace shell 240 in direction D4 (or circumferential direction CD2) thus contracting expandable intervertebral fusion implant 210. It should be appreciated that while wedging component 224 is generally shown having a circular cross-section, wedging component 224 may comprise any geometry suitable for displacing shell 240 with respect to superior component 160, for example, triangular prism, rectangular prism, square prism, wedge-shaped or wedge prism, ovular prism, etc. Wedging component 224 allows the proximal end of expandable intervertebral fusion implant 210 to be expanded after (or before) insertion into a disc space. Any suitable means for displacing wedging component 224 in direction D1 and direction D2 may be used.

In the fully collapsed state, as best shown in FIG. 10A, wedging component 222 is arranged at the distal end of expandable intervertebral fusion implant 210 (i.e., right side) such that surface 232 is spaced apart from surface 176 by height H5. In some embodiments, height H5 is the height of wedging component 222. Wedging component 224 is arranged at the proximal end of expandable intervertebral fusion implant 210 (i.e., left side) such that surface 242 is spaced apart from surface 176 by height H6. In some embodiments, height H6 is the height of wedging component 224. In some embodiments, height H6 is equal to height H5. In some embodiments, height H6 is not equal to height H5.

To expand expandable intervertebral fusion implant 210, wedging component 222 is displaced in direction D1 thereby displacing shell 230 in direction D3 (or circumferential direction CD2), thus expanding the distal end of expandable intervertebral fusion implant 210. Wedging component 224 is displaced in direction D2 thereby displacing shell 240 in direction D3 (or circumferential direction CD1).

FIG. 10B shows expandable intervertebral fusion implant 210 in an expanded state. As shown, wedging component 222 has been displaced in direction D1 forcing shell 230 in direction D3 (or circumferential direction CD2) such that surface 232 is spaced apart from surface 176 by height H7. Height H7 is greater than height H5. Wedging component 224 has been displaced in direction D2 forcing shell 240 in direction D3 (or circumferential direction CD1) such that surface 242 is spaced apart from surface 176 by height H8. Height H8 is greater than height H6. In some embodiments, height H8 is equal to height H7. In some embodiments, height H8 is not equal to height H7. To contract expandable intervertebral fusion implant 210, wedging component 222 is displaced in direction D2, allowing shell 230 to collapse in direction D4 (or circumferential direction CD1). Wedging component 224 is displaced in direction D1, allowing shell 240 to collapse in direction D4 (or circumferential direction CD2).

Figure 11:
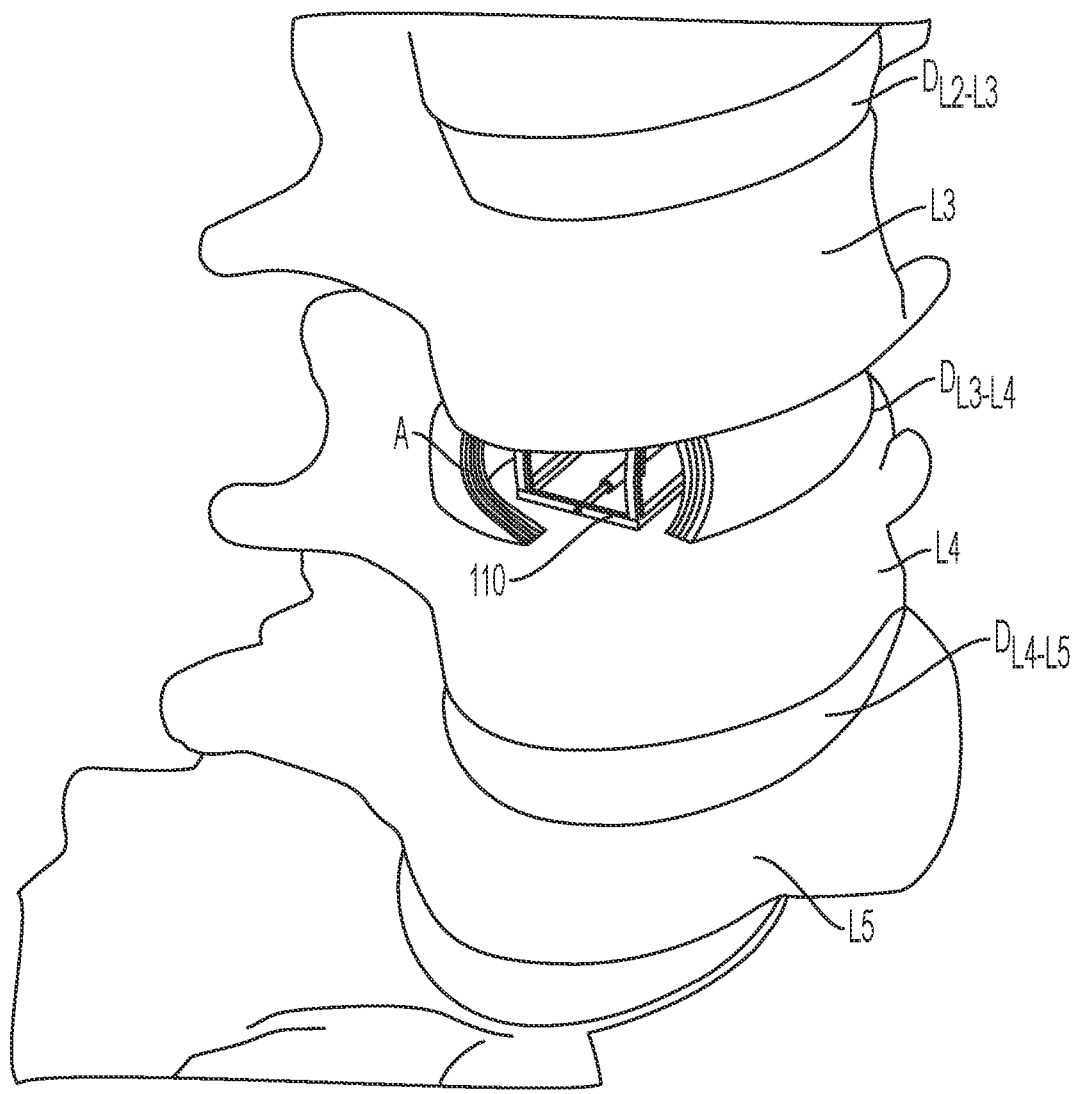

FIG. 11 is an anterior perspective view of a spinal column including expandable intervertebral fusion implant 110, in an expanded state. Expandable intervertebral fusion implant 110 is inserted into the spinal column between, for example, vertebra L3 and vertebra L4, or where disc $D_{L3-L4}$ should be. Expandable intervertebral fusion implant 110 is then vertically expanded until the desired height is reached. As previously described, expandable intervertebral implant 110 is expanded by rotating screw 150 and/or screw 190, or using an expander that forces members 130 and 170 apart. It should be appreciated that expandable intervertebral implant 110 may be expanded prior to insertion, or after insertion. Expandable intervertebral implant 110 is then filled with fusion material, and left in situ.

It will be appreciated that various aspects of the disclosure above and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

REFERENCE NUMERALS

10 Spinal column
12 Ligament
C1-C7 Cervical vertebrae
T1-T12 Thoracic vertebrae
L1-L5 Lumbar vertebrae
S Sacrum
C Coccyx
$D_{L1-L2}$ Disc
$D_{L2-L3}$ Disc
$D_{L3-L4}$ Disc
$D_{L4-L5}$ Disc
F Facet
FJ Facet joint
SP Spinous process
TP Transverse process
IF Intervertebral foramen
NC Neural canal
A Annulus
N Nucleus
DH Disc space height
110 Expandable intervertebral fusion implant
120 Inferior component
122A Longitudinal member
122B Longitudinal member
124A Vertical member
124B Vertical member
126A Vertical member
126B Vertical member
128A Teeth
128B Teeth
130 Horizontal member
132 Hole
134 Horizontal member
136 Surface
138A Hinge component
138B Hinge component
140 Shell
142 Surface
144 Surface
146 Flange
148A Hinge component
148B Hinge component
150 Screw
152 Wedging component
154 Sleeve
160 Superior component
162A Longitudinal member
162B Longitudinal member
164A Vertical member
164B Vertical member
166A Vertical member
166B Vertical member
168A Teeth
168B Teeth
170 Horizontal member
172 Hole
174 Horizontal member
176 Surface
178A Hinge component
178B Hinge component
180 Shell
182 Surface
184 Surface
186 Flange
188A Hinge component
188B Hinge component
190 Screw
192 Wedging component
194 Sleeve
200A Pin
200B Pin
202A Pin
202B Pin
204A Pin
204B Pin
210 Expandable intervertebral fusion implant
220 Hinge
222 Wedging component
224 Wedging component
230 Shell
232 Surface
234 Surface
236 Flange
240 Shell
242 Surface
244 Surface
246 Flange
CD1 Circumferential direction
CD2 Circumferential direction
D1 Direction
D2 Direction
D3 Direction
D4 Direction
H1 Height
H2 Height H3 Height
H4 Height
H5 Height
H6 Height
H7 Height
H8 Height

What is claimed is:

1. An expandable intervertebral fusion implant, comprising:
an inferior component, including:
a first horizontal member;
a first vertical member connected to the first horizontal member; and,
a first outward facing surface;
a superior component hingedly connected to the inferior component, the superior component including:
a second horizontal member;
a second vertical member connected to the second horizontal member; and,
a second outward facing surface directed away from the first outward facing surface;
a first shell hingedly connected to the first outward facing surface; and,
a first wedging component slidingly arranged between the first shell and the first outward facing surface.

2. The expandable intervertebral fusion implant as recited in claim 1, wherein:
the first vertical member is arranged at a proximal end of the inferior component; and,
the first shell is hingedly connected to the inferior component at the proximal end of the inferior component.

3. The expandable intervertebral fusion implant as recited in claim 2, wherein:
the first vertical member comprises a first plurality of teeth;
the second vertical member comprises a second plurality of teeth; and,
the second plurality of teeth are operatively arranged to engage the first plurality of teeth to lock the superior component with respect to the inferior component.

4. The expandable intervertebral fusion implant as recited in claim 2, wherein when the first wedging component is displaced in a first direction with respect to the first outer surface, the first shell is displaced away from the first outer surface.

5. The expandable intervertebral fusion implant as recited in claim 4, further comprising a first screw engaged with the first wedging component, wherein when the first screw is rotated in a first rotational direction the first wedging component is displaced in the first direction.

6. The expandable intervertebral fusion implant as recited in claim 1, further comprising:
a second shell hingedly connected to the superior component; and,
a second wedging component slidingly arranged between the second shell and the second outward facing surface.

7. The expandable intervertebral fusion implant as recited in claim 1, further comprising:
a second shell hingedly connected to the inferior component; and,
a second wedging component slidingly arranged between the second shell and the first outward facing surface.

8. The expandable intervertebral fusion implant as recited in claim 7, wherein:
when the first wedging component is displaced in a first direction with respect to the first outer surface, the first shell is displaced away from the first outer surface; and,
when the second wedging component is displaced in a second direction with respect to the first outer surface, opposite the first direction, the second shell is displaced away from the first outer surface.

9. An expandable intervertebral fusion implant, comprising:
an inferior component, including:
a first horizontal member including a first proximal end and a first distal end;
a first vertical member connected to the first proximal end;
a second vertical member connected to the first distal end; and,
a first outward facing surface;
a superior component, including:
a second horizontal member including a second proximal end and a second distal end;
a third vertical member connected to the second proximal end;
a fourth vertical member connected to the second distal end, the fourth vertical member hingedly connected to the second vertical member; and,
a second outward facing surface directed away from the first outward facing surface;
a first shell hingedly connected to the inferior component; and,
a first wedging component slidingly arranged between the first shell and the first outward facing surface, the first wedging component displaceable along the first outward facing surface.

10. The expandable intervertebral fusion implant as recited in claim 9, wherein the first shell is hingedly connected to the inferior component at the first proximal end.

11. The expandable intervertebral fusion implant as recited in claim 10, wherein:
the first vertical member comprises a first plurality of teeth;
the third vertical member comprises a second plurality of teeth; and,
the second plurality of teeth are operatively arranged to engage the first plurality of teeth to lock the superior component with respect to the inferior component.

12. The expandable intervertebral fusion implant as recited in claim 10, wherein when the first wedging component is displaced in a first direction with respect to the first outer surface, the first shell is displaced away from the first outer surface.

13. The expandable intervertebral fusion implant as recited in claim 12, further comprising a first screw engaged with the first wedging component, wherein when the first screw is rotated in a first rotational direction the first wedging component is displaced in the first direction.

14. The expandable intervertebral fusion implant as recited in claim 9, further comprising:
a second shell hingedly connected to the superior component; and,
a second wedging component slidingly arranged between the second shell and the second outward facing surface.

15. The expandable intervertebral fusion implant as recited in claim 9, further comprising:
a second shell hingedly connected to the inferior component; and,
a second wedging component slidingly arranged between the second shell and the first outward facing surface.

16. The expandable intervertebral fusion implant as recited in claim 15, wherein:

when the first wedging component is displaced in a first direction with respect to the first outer surface, the first shell is displaced away from the first outer surface; and, when the second wedging component is displaced in a second direction with respect to the first outer surface, opposite the first direction, the second shell is displaced away from the first outer surface.

17. An expandable intervertebral fusion implant, comprising:
an inferior component, including:
a first horizontal member including a first proximal end and a first distal end;
a first vertical member connected to the first proximal end and comprising a first plurality of teeth;
a first outward facing surface;
a superior component, including:
a second horizontal member including a second proximal end and a second distal end, the second distal end being pivotably connected to the first distal end;
a second vertical member connected to the second proximal end and including a second plurality of teeth, the second plurality of teeth operatively arranged to engage the first plurality of teeth to prevent displacement of the superior component toward the inferior component; and,
a second outward facing surface directed away from the first outward facing surface;
a first shell hingedly connected to the inferior component; and,
a first wedging component slidingly arranged between the first shell and the first outward facing surface.

18. The expandable intervertebral fusion implant as recited in claim 17, wherein the first shell is hingedly connected to the inferior component at the first proximal end.

19. The expandable intervertebral fusion implant as recited in claim 17, wherein when the first wedging component is displaced in a first direction with respect to the first outer surface, the first shell is displaced away from the first outer surface.

20. The expandable intervertebral fusion implant as recited in claim 19, further comprising:
a second shell hingedly connected to the superior component; and,
a second wedging component slidingly arranged between the second shell and the second outward facing surface, wherein as the second wedging component is displaced in the first direction the second shell is displaced away from the second outer surface.

* * * * *